US009795156B2

(12) United States Patent
Shi et al.

(10) Patent No.: US 9,795,156 B2
(45) Date of Patent: Oct. 24, 2017

(54) REBAUDIOSIDE B AND DERIVATIVES

(75) Inventors: Jingang Shi, Beijing (CN); Hansheng Wang, Taiyuan (CN); Mingming Deng, Beijing (CN); Jien Ding, Shandong (CN); Yanyan Wu, Beijing (CN)

(73) Assignee: E.P.C (Beijing) Plant Pharmaceutical Technology Co., Ltd, Beijing (CN)

( * ) Notice: Subject to any disclaimer, the term of this patent is extended or adjusted under 35 U.S.C. 154(b) by 0 days.

(21) Appl. No.: 13/422,170

(22) Filed: Mar. 16, 2012

(65) Prior Publication Data
US 2013/0071537 A1 Mar. 21, 2013

Related U.S. Application Data

(60) Provisional application No. 61/453,642, filed on Mar. 17, 2011.

(51) Int. Cl.
| A23L 1/236 | (2006.01) |
| A23G 3/00 | (2006.01) |
| C07H 1/00 | (2006.01) |
| C07H 15/256 | (2006.01) |
| A23L 27/30 | (2016.01) |

(52) U.S. Cl.
CPC ............ *A23L 1/2366* (2013.01); *A23L 27/36* (2016.08); *C07H 1/00* (2013.01); *C07H 15/256* (2013.01)

(58) Field of Classification Search
CPC ........ A23L 1/2366; C07H 15/256; C07H 1/00
USPC ................. 426/548, 658; 536/18.1
See application file for complete search history.

(56) References Cited

U.S. PATENT DOCUMENTS

| 3,529,602 | A | | 9/1970 | Hind et al. | |
| 3,703,177 | A | | 11/1972 | Hind et al. | |
| 4,082,858 | A | | 4/1978 | Morita et al. | |
| 4,353,889 | A | | 10/1982 | DuBois | |
| 4,361,697 | A | | 11/1982 | Dobberstein et al. | |
| 4,381,402 | A | * | 4/1983 | DuBois | ............... 560/6 |
| 4,454,290 | A | * | 6/1984 | DuBois | ............... 536/18.1 |
| 4,612,942 | A | | 9/1986 | Dobberstein et al. | |
| 4,892,938 | A | | 1/1990 | Giovanetto | |
| 5,112,610 | A | | 5/1992 | Kienle | |
| 5,753,630 | A | * | 5/1998 | Zopf | ....... A61K 31/70 514/24 |
| 5,962,678 | A | | 10/1999 | Payzant et al. | |
| 5,972,120 | A | | 10/1999 | Kutowy et al. | |
| 6,096,870 | A | | 8/2000 | Mozaffar et al. | |
| 7,238,379 | B2 | | 7/2007 | Lang | |
| 7,923,552 | B2 | | 4/2011 | Jackson et al. | |
| PP22,593 | P3 | | 3/2012 | Garnighian | |
| 8,153,563 | B2 | | 4/2012 | Morgan et al. | |
| 8,257,948 | B1 | | 9/2012 | Markosyan | |
| PP23,164 | P3 | | 11/2012 | Alvarez Britos | |
| 8,318,459 | B2 | | 11/2012 | Markosyan | |
| 8,367,138 | B2 | | 2/2013 | Prakash et al. | |
| 2003/0138538 | A1 | | 7/2003 | Kitazume et al. | |
| 2003/0139610 | A1 | | 7/2003 | Khare et al. | |
| 2006/0083838 | A1 | | 4/2006 | Jackson et al. | |
| 2006/0134292 | A1 | | 6/2006 | Abelyan et al. | |
| 2006/0142555 | A1 | | 6/2006 | Jonnala et al. | |
| 2007/0003679 | A1 | | 1/2007 | Shimizu et al. | |
| 2007/0082103 | A1 | | 4/2007 | Magomet et al. | |
| 2007/0116823 | A1 | * | 5/2007 | Prakash et al. | ............... 426/548 |
| 2007/0116835 | A1 | | 5/2007 | Prakash et al. | |
| 2007/0128311 | A1 | | 6/2007 | Prakash et al. | |
| 2007/0149608 | A1 | * | 6/2007 | Yasuma | ........... C07C 59/68 514/424 |
| 2007/0292582 | A1 | | 12/2007 | Prakash et al. | |
| 2008/0026111 | A1 | | 1/2008 | Bellody et al. | |
| 2008/0300402 | A1 | | 12/2008 | Yang et al. | |
| 2010/0099640 | A1 | * | 4/2010 | Geuns et al. | ........... 514/34 |
| 2010/0099857 | A1 | | 4/2010 | Evans | |
| 2010/0112156 | A1 | | 5/2010 | Abelyan et al. | |
| 2010/0137569 | A1 | | 6/2010 | Prakash et al. | |
| 2010/0316782 | A1 | * | 12/2010 | Shi et al. | ............... 426/548 |
| 2011/0195161 | A1 | | 8/2011 | Upreti et al. | |
| 2012/0058236 | A1 | | 3/2012 | Fosdick et al. | |
| 2012/0058247 | A1 | | 3/2012 | Shi | |
| 2012/0090062 | P1 | | 4/2012 | Alvarez Britos | |
| 2012/0090063 | P1 | | 4/2012 | Alvarez Britos | |
| 2012/0184500 | A1 | | 7/2012 | Goralczyk et al. | |
| 2012/0214751 | A1 | | 8/2012 | Markosyan | |
| 2012/0214752 | A1 | | 8/2012 | Markosyan | |

(Continued)

FOREIGN PATENT DOCUMENTS

| AU | 2004/202670 | 1/2005 |
| CA | 2 185 496 | 3/1998 |

(Continued)

OTHER PUBLICATIONS

M. S. Ahmed, R. H. Dobberstein and N. R.Farnsworth Use of p-bromophenacyl bromide to enhance the detection of water soluble organic acids (Steviolbioside and Rebaudioside B) in High Performance Liquid Chromatography Analysis. Journal of Chromatography, 192 (1980) 387-393.*
Grant E. DuBois Rebecca A, Stephenson Diterpenoid Sweeteners. Synthesis and Sensory Evaluation of Stevioside Analogues with Improved Organoleptic Properties J. Med. Chem. 1985,28,93-98.*
Carakostas et al. in "steviol glycosides" in Alternative sweeteners, 4th edition, p. 161, CRC press 2011.*
Crammer, B. and Ikan, R. "Progress in the chemistry and properties of rebaudiosides," In Developments in Sweeteners-3, T.H. Grenby (ed), Elsevier Applied Science, London, pp. 45-64 (1987).
J.E. Brendle, et al., "Steviol Glycoside Biosynthesis", Phytochemistry 68, 2007, 1855-1863.
International Search Report from PCT/US2008/000700, mailed Jul. 31, 2008, 5 pages.

(Continued)

*Primary Examiner* — Subbalashmi Prakash
(74) *Attorney, Agent, or Firm* — Michael Ye; Andrews Kurth Kenyon LLP

(57) ABSTRACT

The invention describes compositions that include a stevia sweetener and a salt of a steviol glycoside, wherein the concentration of the components provide an improved taste profile where bitterness, after taste and/or lingering of the stevia sweetener is decreased or eliminated.

4 Claims, No Drawings

(56) References Cited

U.S. PATENT DOCUMENTS

| | | |
|---|---|---|
| 2012/0269954 A1 | 10/2012 | Bridges et al. |
| 2012/0282389 A1 | 11/2012 | Purkayastha et al. |
| 2012/0301589 A1 | 11/2012 | Markosyan |
| 2013/0071537 A1 | 3/2013 | Shi et al. |
| 2013/0274351 A1 | 10/2013 | Markosyan et al. |

FOREIGN PATENT DOCUMENTS

| | | |
|---|---|---|
| CN | 1192447 | 9/1998 |
| CN | 1238341 | 12/1999 |
| CN | 1243835 | 2/2000 |
| CN | 101220062 | 7/2001 |
| CN | 1078217 C | 1/2002 |
| CN | 1535607 | 10/2004 |
| CN | 101062078 | 10/2007 |
| CN | 101200480 | 6/2008 |
| CN | 101330833 | 12/2008 |
| CN | 101472487 | 7/2009 |
| CN | 101662955 | 3/2010 |
| CN | 101801177 | 8/2010 |
| CN | 101854814 | 10/2010 |
| EP | 2 215 914 | 8/2010 |
| EP | 2 415 358 | 2/2012 |
| EP | 2 428 123 | 3/2012 |
| EP | 2 456 450 | 5/2012 |
| EP | 2 457 450 | 5/2012 |
| EP | 2 460 419 | 6/2012 |
| EP | 2 486 806 | 8/2012 |
| FR | 2 968 170 | 6/2012 |
| JP | 52-023100 | 2/1977 |
| JP | 52-062300 | 5/1977 |
| JP | 52-83731 A † | 7/1977 |
| JP | 52083731 A * | 7/1977 |
| JP | 54-041898 | 4/1979 |
| JP | 54-041899 | 4/1979 |
| JP | 54-041900 | 4/1979 |
| JP | 55-092400 | 7/1980 |
| JP | 56-121453 | 9/1981 |
| JP | 56-121454 | 9/1981 |
| JP | 56-121455 | 9/1981 |
| JP | 57-086264 | 5/1982 |
| JP | 58-101660 | 6/1983 |
| JP | 58101660 A * | 6/1983 |
| JP | 59120073 | 11/1984 |
| JP | 62-146599 | 6/1987 |
| JP | 63-173531 | 7/1988 |
| JP | 2-261359 | 10/1990 |
| JP | 6-192283 | 7/1994 |
| JP | 7-143860 | 6/1995 |
| JP | 7-177862 | 7/1995 |
| JP | 08-000214 | 1/1996 |
| JP | 08-325156 | 10/1996 |
| JP | 11-243906 | 9/1999 |
| JP | 2002-45145 | 2/2002 |
| JP | 2002-262822 | 9/2002 |
| JP | 2004-344071 | 12/2004 |
| JP | 2012-005483 | 1/2012 |
| JP | 2012-090629 | 5/2012 |
| KR | 1996-0016568 | 12/1996 |
| KR | 2004-0026747 | 4/2004 |
| WO | WO 00/49895 | 8/2000 |
| WO | WO 03/003994 | 1/2003 |
| WO | WO 03-033097 | 4/2003 |
| WO | WO 2006-038221 | 4/2006 |
| WO | WO 2006-045023 | 4/2006 |
| WO | WO 2006-072921 | 7/2006 |
| WO | WO 2006/095366 | 9/2006 |
| WO | WO 2007/061810 | 5/2007 |
| WO | WO 2007/061898 A1 | 5/2007 |
| WO | WO 2008/057968 | 5/2008 |
| WO | WO 2008/091547 | 7/2008 |
| WO | WO 2008/147725 | 12/2008 |
| WO | WO 2009/086049 | 7/2009 |
| WO | WO 2009/140394 A1 | 11/2009 |
| WO | WO 2010/150930 | 12/2010 |
| WO | WO 2011/059954 | 5/2011 |
| WO | WO 2011/094423 | 8/2011 |
| WO | WO 2011/161027 | 12/2011 |
| WO | WO 2012/031879 | 3/2012 |
| WO | WO 2012/006742 | 5/2012 |
| WO | WO 2012/057575 | 5/2012 |
| WO | WO 2012/068457 | 5/2012 |
| WO | WO 2012/073121 A2 | 6/2012 |
| WO | WO 2012/082677 | 6/2012 |
| WO | WO 2012/089861 | 7/2012 |
| WO | WO 2012/102769 | 8/2012 |
| WO | WO 2012/108894 | 8/2012 |
| WO | WO 2012/109506 | 8/2012 |
| WO | WO 2012/112177 | 8/2012 |
| WO | WO 2012/112180 | 8/2012 |
| WO | WO 2012/134502 | 10/2012 |
| WO | WO 2012/153339 | 11/2012 |
| WO | WO 2012/166163 | 12/2012 |
| WO | WO 2012/166164 | 12/2012 |
| WO | WO 2013/036366 | 3/2013 |
| WO | WO 2013/123281 | 8/2013 |

OTHER PUBLICATIONS

International Search Report from PCT/IB2010/001636, mailed Dec. 2, 2010, 4 pages.
International Search Report from PCT/IB2010/003045, mailed May 5, 2011, 4 pages.
Extended European Search Report from related PCT Application PCT/IB2010/003045, dated May 6, 2013, 5 pages.
International Search Report and Written Opinion from PCT/IB2011/003351, dated Jul. 26, 2012, 5 pages.
International Preliminary Report on Patentability from related PCT Application PCT/IB2011/002636, dated Feb. 26, 2013, 5 pages.
International Search Report from related PCT Application PCT/US2012/029613, dated Feb. 1, 2013.
Abou-Arab, et al., "Physico-chemical assessment of natural sweeteners steviosides produced from Stevia rebaudiana bertoni plant" African Journal of Food Science vol. 4(5), May 2010, pp. 269-281.
Serajuddin, "Salt formation to improve drug solubility", Advanced Drug Delivery Reviews 59 (2007) 603-616.
Shibata, et al., "Glucosylation of Steviol and Steviol-Glucosides in Extracts from Stevia rebaudiana Bertoni", Plant Physiol., 1991, vol. 95, pp. 152-156.
Upreti, et al. "Solubility Enhancement of Steviol Glycosides and Characterization of Their Inclusion Complex with Gamma-Cyclodextrin", Int. J. Mol. Sci. Nov. 2011, vol. 12, pp. 7259-7553.
Extended European Search Report from related European Application No. 10789086.5, dated Jun. 6, 2014, 12 pages.
Extended European Search Report from related European Application No. 12756924.2, dated Feb. 6, 2015, 6 pages.
Makapugay, et al., "Improved high-performance liquid chromatographic separation of the Stevie rebaudiana sweet diterpene glycosides using linear gradient elution", Journal of Chromatography, No. 283, 1984, pp. 390-395.
Extended European Search Report from related European Application No. 11844323.3, dated Feb. 11, 2015, 8 pages.
Kasai, et al., "Synthesis of Sweet Diterpene-Glycoside of Leaves of Stevia: rebaudiosides-A,-D, -E and their relating glycosides as well as Relationship between their Sweetness and Chemical Structure", Journal of Chemical Society of Japan, No. 5, 1981, pp. 726-735.
Kinghorn, et al., "Studies to Identify, Isolate, Develop and test Naturally Occurring Noncariogenic Sweeteners that May be Used as Dietary Sucrose Substitutes", Government Reports and Announcements Index, United States, Chemical Abstracts, 1985, 35 pages.
Kolb, et al., "Analysis of Sweet Diterpene Glycosides from Stevia rebaudiana: Improved HPLC Method", Journal of Agricultural Food Chemistry, vol. 49, 2001, pp. 4538-4541.
Ohtani, et al., "Methods to Improve the Taste of the Sweet Principles of Stevia Rebaudiana", Stevia, The Genus Stevia, Edited by A. Douglas Kinghorn, CRC Press, Print ISBN 978-0-415-26830-1, 2001, pp. 138-159.

(56) References Cited

OTHER PUBLICATIONS

Prakash, et al., "Development of rebiana, a natural, non-caloric sweetener", Food and Chemical Toxicology, No. 46(7), 2008, pp. S75-S82.

Sharma, et al., "Chemistry and in vivo profile of ent-kaurene glycosides of Stevia rebaudianna Bertoni—An overview", Natural Product Radiance, vol. 8(2), 2009, pp. 181-189.

Tanaka, "Improvement of Taste of Natural Sweeteners", Pure & Appl. Chem., vol. 69, No. 4, 1997, pp. 675-683.

International Search Report and Written Opinion from PCT/IB2015/053685, dated Sep. 24, 2015, 14 pages.

\* cited by examiner
† cited by third party

REBAUDIOSIDE B AND DERIVATIVES

CROSS REFERENCE TO RELATED APPLICATIONS

This application claims benefit under 35 U.S.C. §119(e) to U.S. Provisional Patent Application Ser. No. 61/453,642, filed Mar. 17, 2011, entitled "Rebaudioside B and Derivatives", the contents of which is incorporated herein by reference in its entirety.

FIELD OF THE INVENTION

The invention relates generally to compositions of stevia based sweeteners that include a salt form of rebaudioside B. It is believed that the use of salt forms of rebaudioside B helps to eliminate the associated bitter aftertaste associated with stevia sweeteners.

BACKGROUND OF THE INVENTION

Stevia is a genus of about 240 species of herbs and shrubs in the sunflower family (Asteraceae), native to subtropical and tropical South America and Central America.

The species *Stevia rebaudiana* Bertoni, commonly known as sweet leaf, sugarleaf, or simply stevia, is widely grown for its sweet leaves. The leaves have traditionally been used as a sweetener. Steviosides and rebaudiosides are the major constituents of glycosides found in the leaves of the stevia plant.

Stevia extracts generally contain a high percentage of the glycosides of the diterpene steviol. The leaves of *stevia rebaudiana* contain 10 different steviol glycosides. Steviol glycosides are considered high intensity sweeteners (about 250-300 times that of sucrose) and have been used for several years in a number of countries as a sweetener for a range of food products. Stevioside and rebaudioside A are the principal sweetening compounds and generally accompanied by smaller amounts of other steviol glycosides. The taste quality of rebaudioside A is better than stevioside, because of increased sweetness and decreased bitterness (Phytochemistry 68, 2007, 1855-1863).

The structures and chemical abstract service registry numbers for steviol and its glycosides that are the main sweetening agents of the additive steviol glycosides are shown below:

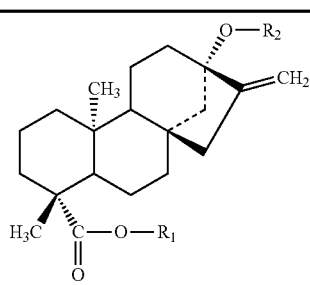

| Compound name | C.A.S. No. | R₁ | R₂ |
| --- | --- | --- | --- |
| 1 Steviol | 471-80-7 | H | H |
| 2 Steviolbioside | 41093-60-1 | H | β-Glc-β-Glc(2→1) |
| 3 Stevioside | 57817-89-7 | β-Glc | β-Glc-β-Glc(2→1) |

-continued

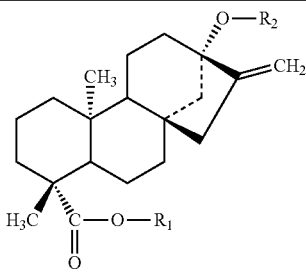

| Compound name | C.A.S. No. | R₁ | R₂ |
| --- | --- | --- | --- |
| 4 Rebaudioside A | 58543-16-1 | β-Glc | β-Glc-β-Glc(2→1)<br>\|<br>β-Glc(3→1) |
| 5 Rebaudioside B | 58543-17-2 | H | β-Glc-β-Glc(2→1)<br>\|<br>β-Glc(3→1) |
| 6 Rebaudioside C | 63550-99-2 | β-Glc | β-Glc-β-Rha(2→1)<br>\|<br>β-Glc(3→1) |
| 7 Rebaudioside D | 63279-13-0 | β-Glc-β-Glc(2→1) | β-Glc-β-Glc(2→1)<br>\|<br>β-Glc(3→1) |
| 8 Rebaudioside E | 63279-14-1 | β-Glc-β-Glc(2→1) | β-Glc-β-Glc(2→1) |
| 9 Rebaudioside F | 438045-89-7 | β-Glc | β-Glc-β-Xyl(2→1)<br>\|<br>β-Glc(3→1) |
| 10 Rubusoside | 63849-39-4 | β-Glc | β-Glc |
| 11 Dulcoside A | 64432-06-0 | β-Glc | β-Glc-α-Rha(2→1) |

Steviol glycoside preparations are generally white to light yellow powders that are freely soluble in water and ethanol. The powders can be odorless or have a slight characteristic odor. Aqueous solutions are 200 to 300 times sweeter than sucrose under identical conditions. With its extracts having up to 300 times the sweetness of sugar, stevia has garnered attention with the rise in demand for low-carbohydrate, low-sugar food alternatives.

Medical research has also shown possible benefits of stevia in treating obesity and high blood pressure. Because stevia has a negligible effect on blood glucose, it is attractive as a natural sweetener to people on carbohydrate-controlled diets.

Stevia sweeteners, for example, rebaudioside A (RA), one of the steviol glycosides, is regarded as a promising substitute of sugar, but it still has some drawbacks. When it is dissolved in an aqueous solution, there is a significant taste profile that differs from sugar, such as slow onset, bitterness and a lingering aftertaste. These drawbacks are some of the reasons that have resulted in unsatisfactory acceptable by consumers for stevia sweeteners, such as RA. The taste profile has become a key barrier to the use of stevia sweeteners in food or beverage applications, even if it has been approved as a food additive by the FDA. It is generally recognized that some impurities in stevia sweeteners are related to the aforementioned disadvantages. In recent years, a great deal of focus has been on obtaining a high purity of RA, from the initial 50%, 80%, 90% to the present 95%, 97%, 99%, up to 100%. However, with regard to 100% purity, sensory tests still show that a 200 ppm aqueous solution cannot bring a perfect taste close to sugar, and bitterness and aftertaste issues appear strongly at higher concentrations, for example, at a 500 ppm concentration. As a sweetener and as a promising sugar substitute, the taste of RA etc. must be further improved in order to meet sensory requirements for its applications in food and beverage, especially for use at high concentrations.

Therefore, a need exists for an improved stevia sweetener that overcomes one or more of the current disadvantages noted above.

BRIEF SUMMARY OF THE INVENTION

The present invention surprisingly finds rebaudioside B (RB) provides the ability to mask, decrease or eliminate bitterness in stevia extract compositions. In particular, compositions that contain steviol glycosides typically have a bitter aftertaste. This masking of the bitterness is by the incorporation of a specific amount of RB, relative to the given composition. Generally this is from about 1 to about 30 weight percent RB to the remaining weight of the composition.

Rebaudioside B (RB) salts are described herein as well as methods to prepare RB salts and solutions of RB salt(s) that can have high concentrations of RB salt(s) and remain stable a low pH values. The salt of RB can be used by itself as a sweetener and is less bitter than other stevia glycosides (excluding RD), such as RA. Alternatively, compositions that include a salt of rebaudioside B, with one or more steviol glycoside(s), such as steviol, steviolbioside, stevioside, rebaudioside A (RA), rebaudioside B (RB), rebaudioside C (RC), rebaudioside D (RD), rebaudioside E (RE), rebaudioside F (RF), rubusoside and dulcoside A are also sweet and have improved taste characteristics over those compositions without the RB salt. The resulting RB salt containing compositions, with or without additional steviol glycosides address one or more of the above-identified current disadvantages of stevia sweeteners.

The present inventors surprisingly found that aqueous salts of RB improves the taste of stevia sweetener compositions. For example, a salt of RB without any additional steviol glycoside(s) or stevia extract(s) acts as a sweetener. Use of a salt of RB in combination with stevia sweeteners improves the taste profile of the combination.

It has also been surprisingly found that a salt of RB, optionally with a steviol glycoside such as RA, remains stable at a pH of about 2.7. This is one important aspect of use of a RB salt since many beverages, such as soda, have an acidic pH profile.

Rebaudioside B (RB) is one of the sweet components of stevia, which can be obtained from stevia leaf by aqueous extraction, or a water-alcohol extraction, as a clear liquid. The purity of RB depends on the type of extraction. The leaves of stevia may differ in quantity depending on several factors, such as climatic conditions, soil type, light, irrigation methods, systems of cultivation, processing and storage. If necessary, a purity of 90% or greater of RB can be provided by the extraction process. Compared with other steviol glycosides, RB has a short on-set profile. Based on the characteristic, RB alone and mixtures containing RB have a potential to be a substitute of the present sweetener. e.g. RA is a good choice to sweeten food or beverage. When RA be used with RB, the food or beverage would provide a better taste, if the customer require shorter on-set profile. Generally, purified RB is applicable to many cases where sweetness and short on set profiles are desired.

In another aspect, it has been surprisingly found that purified RB having a purity of at least 95% (e.g., 96%, 97%, 98%, 99%, 99.5%, 99.9%, 99.99%, 100%) has suitable sweetness but a less bitter taste than RA. Thus combinations of RB with RA, for example, provide a sweetener with a less bitter aftertaste than RA alone. Surprisingly, RB acts synergistically with other sweeteners. This is noted as some literature describes RB as a bitter substance.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The phrase "stevia sweetener" as referred to herein, pertains to a stevia extract that includes one or more steviol glycosides found in the stevia plant, especially, a stevia extract that comprises RA and one or more steviol glycosides found in the stevia plant. These include, but are not limited to components of stevia such as steviol, steviolbioside, stevioside, rebaudioside A (RA), rebaudioside B (RB), rebaudioside C(RC), rebaudioside D (RD), rebaudioside E (RE), rebaudioside F (RF), rubusoside and dulcoside A.

Typically, the stevia sweetener comprises rebaudioside A and rebaudioside D, or rebaudioside A and stevioside, or rebaudioside A and rebaudioside B.

It has been surprisingly found that by increasing the amount of rebaudioside B present in a composition that includes rebaudioside A and/or other stevia components such as steviol glycosides that have an aftertaste, that an increase of about 1% to 30% by weight of rebaudioside B overcomes, decreases, eliminates or masks the aftertaste of rebaudioside A (and/or the components of a given composition that cause an aftertaste). Up until the time of the present disclosure, it had not been appreciated the rebaudioside B could weaken the aftertaste effects of steviol glycosides, such as rebaudioside A. Rebaudioside A is a major component of stevia extracts.

In one aspect, the salt of RB with or without a steviol glycoside, such as RA, remains stable at low pH. The term "stable" refers to the advantage that the salt form of RB retains its taste profile at a pH below 7, in particular below about 6, and particularly below about 3. It appears that stability is also imparted to steviol glycosides, such as RA, when combined with the salt of RB or when present as a salt form of itself (e.g., salt form of RA, salt form of RD, etc.).

Additionally, the lingering profile of stevia sweetener is decreased or eliminated with the inclusion of a salt of RB, with or without one or more surfactants.

Stevia sweeteners, such as rebaudioside A (RA), are suitable substitutes for sugar. However, practical applications of RA are problematic. There is no increased perceived sweetness when RA is added to a food stuff or beverage ("food products") when greater than about 500 ppm of RA are used in the food products.

About 250 ppm RA provides maximum sweetness in an aqueous solution. If the concentration of RA is increased above about 250 ppm, no linear relationship between sweetness and concentration is found.

Some food applications, like sodas, e.g., cola, require a very high sweetness profile, especially at low pH values. For example, comparison between aqueous solutions of 200 ppm and 500 ppm RA demonstrates that sweetness is not increased as the concentration of RA is increased. Consequently, stevia sweetener(s) require a novel approach to achieve increased sweetness at high concentrations of a sweetener.

The salts of rebaudioside B (RB) described herein can be used alone or in combination with various sweeteners to increase sweetness, and/or to reduce or eliminate bitterness, and/or to reduce or eliminate aftertaste, and/or reduce or eliminate lingering aftertaste and/or provide a sweetness profile similar to that of sugar. The novel carboxylic acid salts described herein have the general formula (I):

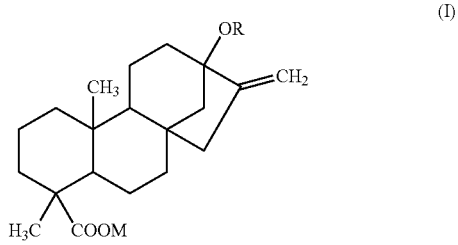

(I)

wherein M is any suitable cation that can replace a hydrogen atom, such as an alkali metal or alkaline earth metal, an amino acid, an ammonium ion, etc. and R is a hydrogen or a sugar moiety.

In one aspect, M is a sodium ion, ammonium, lithium or a potassium ion.

In another aspect, M is a magnesium, calcium, strontium or barium ion.

In one aspect, the sugar of the RB moiety is a monosaccharide or an oligosaccharide. Suitable monosaccharides include, for example, glucose (dextrose), fructose (levulose), galactose, rhamnose, xylose and/or ribose. In another aspect, the sugar can optionally be sucrose, maltose, lactose, -glucose-glucose, -glucose(-glucose)-glucose, -glucose(-rhamnose)-glucose.

Stevia contains some components of steviol, such as those represented by formula (II):

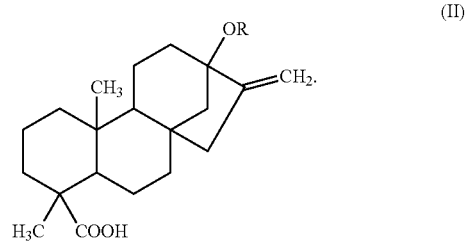

(II)

When the R groups are varied, compounds of Formula II are provided in Table 1.

| R | Formula II |
|---|---|
| Hydrogen | Steviol |
| β-Glc-β-Glc(2→1) | Steviolbioside |
| β-Glc-β-Glc(2→1)<br>\|<br>β-Glc(3→1) | Rebaudioside B |

Steviol and its derivatives, such as rebaudioside B (RB), as natural components in stevia extract, are encompassed by Formula II.

Table 1 lists components that naturally occur in stevia extracts. R can also represent other groups, as a result, the corresponding Formula II is not limited within compounds naturally occurring in stevia. For example, when R is β-Glc, Formula II means steviolmonoside, which does not naturally exist in stevia extract.

Referring now to Formula II, R can be a monosaccharide or an oligosaccharide.

Suitable monosaccharides include glucose (dextrose), fructose (levulose), galactose, rhamnose, xylose and/or ribose.

Suitable oligosaccharides include sucrose, maltose, lactose, -glucose-glucose, -glucose(-glucose)-glucose, -glucose(-rhamnose)-glucose.

For example, when R is -glucose(-glucose)-glucose, and M is potassium, formula I means potassium salt of rebaudioside B.

When R is -glucose(-glucose)-glucose, and M is sodium, Formula I provides the sodium salt of rebaudioside B.

When R is -glucose(-glucose)-glucose, and M is potassium, Formula I provides the potassium salt of rebaudioside B.

Preparation of Carboxylic Acid Salts.

A method is also disclosed herein to prepare the novel compounds as shown in Formula I.

Compounds within the scope of Formula II provide a group of derivatives of steviol, and include a carboxylic acid. Therefore, basic substances, such as amines, amino acids, metal hydroxides and the like, can react with the carboxylic acid. When the basic substance is one of a group including hydroxide ions of M, oxide of M, carbonate of M or bicarbonate of M, and then compounds of Formula I are prepared. Generally, the reaction between the carboxylic acid and base is in an aqueous environment.

Suitable base materials include, but are not limited to oxides of metals, carbonates of metals and bicarbonates of metals. Such materials include, for example, NaOH, KOH, $Na_2O$, $K_2O$, $Na_2CO_3$, $K_2CO_3$, $NaHCO_3$ or $KHCO_3$.

In aqueous environment, carboxylic acid containing steviol glycosides such as steviol, steviolbioside, or rebaudioside B can react with one of the hydroxides of M, oxides of M, carbonates of M or bicarbonates of M, to provide compounds of Formula I.

Under appropriate basic conditions, RA can be converted into RB which in turn can then be converted into a salt of RB. Likewise, rebaudioside D can also be converted into RB.

In view of different processing for food or beverage, simple blends of RA, RB and/or RD with base can achieve the same or similar result as compound of formula I. For example, a blend of RA with KOH (1:1 on a molar basis) undergoes heating process, e.g. high temperature cooking and can have the same effect as using the potassium salt of RebB at the beginning of cooking.

Likewise, steviol glycosides such as rebaudioside C, D, E, F, steviolmonoside, rubusoside and dulcoside A can be hydrolyzed under basic or acidic conditions at the C-19 position to afford a carboxylic acid or carboxylic acid salt.

When preparing a carbonate of M or bicarbonate of M as reactant, the temperature of reaction system is generally performed at a temperature above room temperature.

The salt forms of the steviol glycosides can be isolated and/or purified by known methods, such as by recrystallization, HPLC preparation, column chromatography and the like. Typically, the salt form of the steviol glycoside has a purity of at least 80%, more particularly 90% and even more particularly greater than 95% by weight. Ideally, the salt form of the steviol glycoside has a purity of 96%, 97%, 98%, 99%, 99.5%, 99.9% or greater.

In one aspect, a mixture of RB salt and RA can be effected by appropriate selection of the percentage of base utilized. For example, a 50 mol % of base would provide a mixture of 50% RB salt and 50% RA on a molar basis. As an example, following the procedure of Example 1 vide infra, a mixture of RB salt and RA can be produced. Selection of the amount of base will effect the overall percentage of RB salt in the mixture and can be varied from about 1 mol % base to 100 mol % base, where 100 mol % base would convert all of RA into an RB salt. In one embodiment, the mixture would provide 50% RB salt and 50% RA. This ratio, of course, can be varied depending upon the amount of base utilized.

Technical Effect

The compounds (the salts) described herein, especially salts of rebaudioside B (RB), are high potency sweeteners, having good potency to provide increased sweetness at higher concentrations of the stevia material from which it is derived. Therefore, the present invention solves the problem, for example, where a solution with high concentration of rebaudioside A, from 500 ppm to 1000 ppm, has no increased perceived sweetness than a solution of 300 ppm RA. In other words, the salts described herein provide solutions with higher concentration of stevia sweetener where the perceived sweetness is increased as well.

Perhaps more importantly, the salts described herein are sweeteners by themselves. Many have improved properties over their non-salt forms or non-purified forms, such as the salt of RB. The carboxylic salts can be used then alone or in combination with foodstuffs.

The compounds described herein, especially salts of rebaudioside B, when blending with other stevia sweetener(s) or other sweetener(s) such as RA, produce a composition that is stable at low pH values, such as at pH 2.7.

The compounds described herein, especially salts of rebaudioside B, can also be blended with other sweetener(s) to form new sweetener compositions. Such compositions have reduced or eliminated after taste and/or bitterness associated with typical stevia sweeteners or stevia extracts.

To avoid destroying an RB salt's nature, such as food safety, its natural qualities, and zero calorie aspects, the potential candidates of surfactant should be of corresponding characteristics, like naturally occurring, safe for ingestion, no after taste and/or no caloric content.

As a sweetener, sweet taste acceptance determines market value. Due to bitterness or aftertaste associated with steviol components, there is still a need to eliminate these disadvantages from a stevia sweetener.

The compositions described herein can be used in beverages, broths, and beverage preparations selected from the group comprising carbonated, non-carbonated, frozen, semi-frozen ("slush"), non-frozen, ready-to-drink, concentrated (powdered, frozen, or syrup), dairy, non-dairy, herbal, non-herbal, caffeinated, non-caffeinated, alcoholic, non-alcoholic, flavored, non-flavored, vegetable-based, fruit-based, root/tuber/corm-based, nut-based, other plant-based, cola-based, chocolate-based, meat-based, seafood-based, other animal-based, algae-based, calorie enhanced, calorie-reduced, and calorie-free products, optionally dispensed in open containers, cans, bottles or other packaging. Such beverages and beverage preparations can be in ready-to-drink, ready-to-cook, ready-to-mix, raw, or ingredient form and can use one or more RB salt(s) as a sole sweetener or as a co-sweetener.

The compositions can be used in foods and food preparations (e.g. sweeteners, soups, sauces, flavorings, spices, oils, fats, and condiments) from dairy-based, cereal-based, baked, vegetable-based, fruit-based, root/tuber/corm-based, nut-based, other plant-based, egg-based, meat-based, seafood-based, other animal-based, algae-based, processed (e.g. spreads), preserved (e.g. meals-ready-to-eat rations), and synthesized (e.g. gels) products. Such foods and food preparations can be in ready-to-eat, ready-to-cook, ready-to-mix, raw, or ingredient form and can use one or more RB salt(s) as a sole sweetener or as a co-sweetener.

The compositions described herein can be used in candies, confections, desserts, and snacks selected from the group comprising dairy-based, cereal-based, baked, vegetable-based, fruit-based, root/tuber/corm-based, nut-based, gum-based, other plant-based, egg-based, meat-based, seafood-based, other animal-based, algae-based, processed (e.g. spreads), preserved (e.g. meals-ready-to-eat rations), and synthesized (e.g. gels) products. Such candies, confections, desserts, and snacks can be in ready-to-eat, ready-to-cook, ready-to-mix, raw, or ingredient form, and can use the composition as a sole sweetener or as a co-sweetener.

The composition described herein can be used in prescription and over-the-counter pharmaceuticals, assays, diagnostic kits, and therapies selected from the group comprising weight control, nutritional supplement, vitamins, infant diet, diabetic diet, athlete diet, geriatric diet, low carbohydrate diet, low fat diet, low protein diet, high carbohydrate diet, high fat diet, high protein diet, low calorie diet, non-caloric diet, oral hygiene products (e.g. toothpaste, mouthwash, rinses, floss, toothbrushes, other implements), personal care products (e.g. soaps, shampoos, rinses, lotions, balms, salves, ointments, paper goods, perfumes, lipstick, other cosmetics), professional dentistry products in which taste or smell is a factor (e.g. liquids, chewables, inhalables, injectables, salves, resins, rinses, pads, floss, implements), medical, veterinarian, and surgical products in which taste or smell is a factor (e.g. liquids, chewables, inhalables, injectables, salves, resins, rinses, pads, floss, implements), and pharmaceutical compounding fillers, syrups, capsules, gels, and coating products.

The compositions described herein can be used in consumer goods packaging materials and containers selected from the group comprising plastic film, thermoset and thermoplastic resin, gum, foil, paper, bottle, box, ink, paint, adhesive, and packaging coating products.

The compositions described herein can be used in goods including sweeteners, co-sweeteners, coated sweetener sticks, frozen confection sticks, medicine spoons (human and veterinary uses), dental instruments, pre-sweetened disposable tableware and utensils, sachets, edible sachets, potpourris, edible potpourris, artificial flowers, edible artificial flowers, clothing, edible clothing, massage oils, and edible massage oils.

The compositions described herein can also be used with "artificial sweeteners". Artificial sweeteners are those, other than sucrose, such as cyclamates and salts thereof, sucralose, aspartame, saccharin and salts thereof, stevia (Truvia™), rebaudioside A, xylitol, acesulfame-K and the like.

According to variations in temperature, pH value, concentration, viscosity, etc., the user can choose or adjust kinds, types, other parameters of surfactant to achieve the desired technical purpose, based on the principles of the present invention.

The following paragraphs enumerated consecutively from 1 through 61 provide for various aspects of the present invention. In one embodiment, in a first paragraph (1), the present invention provides a purified compound comprising Formula I:

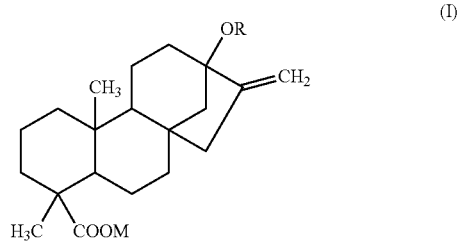

(I)

wherein M is any suitable cation that can replace a hydrogen atom, such as an alkali metal or alkaline earth metal, an amino acid, an ammonium ion, etc.; and R is a hydrogen atom or a sugar.

2. The purified compound according to paragraph 1, wherein M is a sodium or potassium ion.

3. The purified compound according to either paragraphs 1 or 2, wherein the sugar is a monosaccharide or an oligosaccharide.

4. The purified compound according to paragraph 3, wherein the monosaccharide is glucose (dextrose), fructose (levulose), galactose, rhamnose, xylose and/or ribose.

5. The purified compound according to paragraph 3, wherein the oligosaccharide is sucrose, maltose, lactose, -glucose-glucose, -glucose(-glucose)-glucose, -glucose(-rhamnose)-glucose.

6 The purified compound according to paragraph 5, wherein M is a potassium ion and R is glucose(-glucose-)glucose.

7. The purified compound according to paragraph 5, wherein M is a sodium ion and R is glucose(-glucose)-glucose.

8. A process to prepare a carboxylic acid salt of steviol or a steviol glycoside, comprising the step of:
reacting steviol or a steviol glycoside with a base, such that a carboxylic acid salt is formed.

9. The process of paragraph 8, wherein the ratio of base to possible carboxylic acid content is 1:1.

10. The process of paragraph 8, wherein the ratio of base to possible carboxylic acid content is at least 10 molar percent.

11. The process of any of paragraphs 8 through 10, wherein the base is an amine, an amino acid, a metal carbonate, a metal bicarbonate, a metal hydroxide or a metal oxide.

12. The process of any of paragraphs 8 through 11, wherein the process is conducted in an aqueous environment.

13. The process of any of paragraphs 8 through 12, wherein the process is conducted at a temperature of at least about 30° C. to about reflux.

14. The process of any of paragraphs 8 through 13, wherein the carboxylic acid salt is isolated.

15. The process of any of paragraphs 8 through 14, wherein the steviol glycoside is rebaudioside A, B, C, D, E, F, stevioside, steviolmonoside, steviolbioside, rubusoside, dulcoside A or mixtures thereof.

16. The process of any of paragraphs 8 through 14, wherein the steviol glycoside is raudioside A, B, D or mixtures thereof.

17. A process to prepare a carboxylic acid salt of a stevia extract, comprising the step of:
reacting the stevia extract with a base, such that a carboxylic acid salt is formed with one or more constituents of the stevia extract.

18. The process of paragraph 17, wherein the stevia extract constituents comprise one or more of rebaudioside A, B, C, D, E, F, stevioside, steviolmonoside, steviolbioside, rubusoside, dulcoside A or mixtures thereof.

19. The process of paragraph 17, wherein the stevia extract constituents comprise one or more of raudioside A, B, D or mixtures thereof.

20. The process of any of paragraphs 17 through 19, wherein the ratio of base to possible carboxylic acid content is 1:1.

21. The process of any of paragraph 17 through 19, wherein the ratio of base to possible carboxylic acid content is at least 10 molar percent.

22. The process of any of paragraphs 17 through 21, wherein the base is an amine, an amino acid, a metal carbonate, a metal bicarbonate, a metal hydroxide or a metal oxide.

23. The process of any of paragraphs 17 through 22, wherein the process is conducted in an aqueous environment.

24. The process of any of paragraphs 17 through 23, wherein the process is conducted at a temperature of at least about 30° C. to about reflux.

25. The process of any of paragraphs 17 through 24, wherein the carboxylic acid salt is/are isolated.

26. A process to prepare the compound of Formula I of any of paragraphs 1 through 7, comprising the step of:
reacting one or more of steviol or a steviol glycoside with an amine, an amino acid, a hydroxide of M, oxide of M, carbonate of M or bicarbonate of M.

27. The process according to paragraph 26, wherein the steviol glycoside is rebaudioside A, B, C, D, E, F, stevioside, steviolmonoside, steviolbioside, rubusoside, dulcoside A or mixtures thereof.

28. The process according to either paragraph 26 or 27, wherein M is potassium or sodium.

29. The process according to any of paragraphs 26, 27 or 28, wherein the reaction takes place in an aqueous environment.

30. The process according to any of paragraphs 26 through 29, further including heating the reaction mixture to a temperature of at least about 30° C. to about reflux.

31. A sweetener composition comprising the compound as paragraphed in any of paragraphs 1 through 7 and a sweetener.

32. The sweetener composition according to paragraph 31, wherein the sweetener is a purified extract of stevia or mogroside V.

33. The sweetener composition according to paragraph 32, wherein the purified extract of stevia comprises rebaudioside A ranging from about 50% to about 100%.

34. The sweetener composition according to paragraph 33, wherein the purified extract of stevia comprises rebaudioside A ranging from about 95% to about 100%.

35. The sweetener composition according to any of paragraphs 32 through 34, wherein the ratio of the purified extract of stevia to compound as in paragraphs 1 through 7 is from about 6:4 to about 95:5.

36. The sweetener composition according to paragraph 35, wherein the ratio is about 7:3.

37. A purified rebaudioside B (RB) sweetener consisting essentially of RB.

38. The purified rebaudioside B (RB) sweetener of paragraph 37, wherein the purity of the RB is 99% or greater.

39. The purified rebaudioside B (RB) sweetener of either paragraphs 37 or 38, wherein any detected bitterness is less than rebaudioside A (RA).

40. A mixture of a rebaudioside B carboxylic acid salt and rebaudioside A.

41. The mixture of paragraph 40, wherein the ratio is from about 1:9 to about 9:1 on a molar basis.

42. The mixture of either paragraph 40 or 41, wherein the salt is a sodium or potassium salt.

43. A mixture of a rebaudioside B carboxylic acid salt and a stevia extract.

44. The mixture of paragraph 43, wherein the ratio is from about 1:9 to about 9:1 on a weight basis.

45. The mixture of either paragraph 42 or 43, wherein the salt is a sodium or potassium salt.

46. A mixture of a rebaudioside B carboxylic acid salt and one or more of rebaudioside A, B, C, D, E, F, stevioside, steviolmonoside, steviolbioside, rubusoside, dulcoside or mixtures thereof.

47. The mixture of paragraph 46, wherein the ratio is from about 1:9 to about 9:1 on a molar basis.

48. The mixture of either paragraph 46 or 47, wherein the salt is a sodium or potassium salt.

49. A mixture of consisting essentially of rebaudioside A and rebaudioside B.

50. The mixture of paragraph 49, wherein the ratio is about 1:1 on a weight basis.

51. The mixture of any either paragraphs 49 or 50, wherein the RA has a purity of at least 95% by HPLC and RB has a purity of at least 95% by HPLC.

52. A mixture of rebaudioside A and rebaudioside B, wherein one or more of rebaudioside C, D, E, F, stevioside, steviolmonoside, steviolbioside, rubusoside, or dulcoside is absent from the mixture.

53. The mixture of paragraph 52, wherein the RA has a purity of at least 95% by HPLC and RB has a purity of at least 95% by HPLC.

54. A mixture of RB and one of rebaudioside C, D, E, F, stevioside, steviolmonoside, steviolbioside, rubusoside, or dulcoside.

55. The mixture of paragraph 54, wherein RB has a purity of at least 95% by HPLC.

56. A sweetener composition comprising one or more of RB, RA, or RD with a base.

57. The composition according to paragraph 56, wherein the base is an amine, a metal hydroxide, a metal oxide, an amino acid, a metal carbonate or a metal bicarbonate.

58. The composition according to paragraph 57, wherein the base is a metal hydroxide.

59. The composition according to paragraph 58, wherein the metal is alkali metal or alkaline earth metal.

60. The composition according to paragraph 59, wherein the alkali metal is sodium or potassium.

61. The composition according to any of paragraphs 56-60, wherein the rebaudioside to base ratio is from about 10:1 to 1:10 on molar basis.

The following paragraphs enumerated consecutively from 8 through 25 provide for additional aspects of the present invention. In one embodiment, in paragraph 8 a mixture consisting essentially of rebaudioside A (RA) and rebaudioside B (RB).

9. The mixture of paragraph 8, wherein the ratio of RA to RB is from 70:30 to 99:1 by weight.

10. The mixture of paragraph 9, wherein the ratio of RA to RB is from 75:25 to 95:5 by weight.

11. The mixture of paragraph 10, wherein the ratio of RA to RB is from 80:20 to 95:5 by weight.

12. The mixture of paragraph 11, wherein the ratio of RA to RB is from 85:15 to 95:5 by weight.

13. The mixture of paragraph 12, wherein the ratio of RA to RB is about 90:10 by weight.

14. The mixture of paragraph 13, wherein the mixture further contains rebaudioside D.

15. The mixture of paragraph 14, wherein the ratio of RD to RA is from 30:70 to 5:95 by weight.

16. A sweetener composition comprising one or more of RB, RA, or RD with a base.

17. The composition according to paragraph 16, wherein the base is an amine, a metal hydroxide, a metal oxide, an amino acid, a metal carbonate or a metal bicarbonate.

18. The composition according to paragraph 17, wherein the base is a metal hydroxide.

19. The composition according to paragraph 18, wherein the metal is alkali metal or alkaline earth metal.

20. The composition according to paragraph 19, wherein the alkali metal is sodium or potassium.

21. The composition according to paragraph 16, wherein the rebaudioside to base ratio is from about 10:1 to 1:10 on molar basis.

22. The composition according to paragraph 17, wherein the rebaudioside to base ratio is from about 10:1 to 1:10 on molar basis.

23. The composition according to paragraph 18, wherein the rebaudioside to base ratio is from about 10:1 to 1:10 on molar basis.

24. The composition according to paragraph 19, wherein the rebaudioside to base ratio is from about 10:1 to 1:10 on molar basis.

25. The composition according to paragraph 20, wherein the rebaudioside to base ratio is from about 10:1 to 1:10 on molar basis.

The following paragraphs enumerated consecutively from 8 through 17 provide for still more aspects of the present invention. In one embodiment, in paragraph 8, a mixture consisting essentially of stevia extract, wherein the mixture contains about 1% to 30% rebaudioside B (RB) by weight.

9. The mixture of paragraph 8, wherein the stevia extract has above 90% purity of total steviol glycosides.

10. The mixture of paragraph 8, wherein the stevia extract has above 95% purity of total steviol glycosides.

11. The mixture of paragraph 9 or 10, wherein total steviol glycosides contain rebaudioside A (RA) and/or rebaudioside D (RD).

12. The mixture of paragraph 11, wherein the ratio of RA to RB is from 70:30 to 99:1 by weight.

13. The mixture of paragraph 12, wherein the ratio of RA to RB is from 75:25 to 95:5 by weight.

14. The mixture of paragraph 13, wherein the ratio of RA to RB is from 80:20 to 95:5 by weight.

15. The mixture of paragraph 14, wherein the ratio of RA to RB is from 85:15 to 95:5 by weight.

16. The mixture of paragraph 15, wherein the ratio of RA to RB is about 90:10 by weight.

17. The mixture of any of paragraphs 11 through 16, wherein the ratio of RD to RA is from 30:70 to 5:95 by weight.

The following paragraphs enumerated consecutively from 8 through 44 provide for yet still more aspects of the present invention. In one embodiment, in paragraph 8, a mixture consisting essentially of stevia extract, wherein the mixture contains about 1% to 30% rebaudioside B (RB) by weight.

9. The mixture of paragraph 8, wherein the stevia extract has above 90% purity of total steviol glycosides.

10. The mixture of paragraph 8, wherein the stevia extract has above 95% purity of total steviol glycosides.

11. The mixture of paragraph 9, wherein total steviol glycosides contain rebaudioside A (RA) and/or rebaudioside D (RD).

12. The mixture of paragraph 11, wherein the ratio of RA to RB is from 70:30 to 99:1 by weight.

13. The mixture of paragraph 12, wherein the ratio of RA to RB is from 75:25 to 95:5 by weight.

14. The mixture of paragraph 13, wherein the ratio of RA to RB is from 80:20 to 95:5 by weight.

15. The mixture of paragraph 14, wherein the ratio of RA to RB is from 85:15 to 95:5 by weight.

16. The mixture of paragraph 15, wherein the ratio of RA to RB is about 90:10 by weight.

17. The mixture of paragraph 10, wherein total steviol glycosides contain rebaudioside A (RA) and/or rebaudioside D (RD).

18. The mixture of paragraph 17, wherein the ratio of RA to RB is from 70:30 to 99:1 by weight.

19. The mixture of paragraph 18, wherein the ratio of RA to RB is from 75:25 to 95:5 by weight.

20. The mixture of paragraph 19, wherein the ratio of RA to RB is from 80:20 to 95:5 by weight.

21. The mixture of paragraph 20, wherein the ratio of RA to RB is from 85:15 to 95:5 by weight.

22. The mixture of paragraph 21, wherein the ratio of RA to RB is about 90:10 by weight.

23. The mixture of paragraph 11, wherein the ratio of RD to RA is from 30:70 to 5:95 by weight.

24. The mixture of paragraph 12, wherein the ratio of RD to RA is from 30:70 to 5:95 by weight.

25. The mixture of paragraph 13, wherein the ratio of RD to RA is from 30:70 to 5:95 by weight.

26. The mixture of paragraph 14, wherein the ratio of RD to RA is from 30:70 to 5:95 by weight.

27. The mixture of paragraph 15, wherein the ratio of RD to RA is from 30:70 to 5:95 by weight.

28. The mixture of paragraph 16, wherein the ratio of RD to RA is from 30:70 to 5:95 by weight.

29. The mixture of paragraph 17, wherein the ratio of RD to RA is from 30:70 to 5:95 by weight.

30. The mixture of paragraph 18, wherein the ratio of RD to RA is from 30:70 to 5:95 by weight.

31. The mixture of paragraph 19, wherein the ratio of RD to RA is from 30:70 to 5:95 by weight.

32. The mixture of paragraph 20, wherein the ratio of RD to RA is from 30:70 to 5:95 by weight.

33. The mixture of paragraph 21, wherein the ratio of RD to RA is from 30:70 to 5:95 by weight.

34. The mixture of paragraph 22, wherein the ratio of RD to RA is from 30:70 to 5:95 by weight.

35. A sweetener composition comprising one or more of RB, RA, or RD with a base.

36. The composition according to paragraph 35, wherein the base is an amine, a metal hydroxide, a metal oxide, an amino acid, a metal carbonate or a metal bicarbonate.

37. The composition according to paragraph 36, wherein the base is a metal hydroxide.

38. The composition according to paragraph 37, wherein the metal is alkali metal or alkaline earth metal.

39. The composition according to paragraph 38, wherein the alkali metal is sodium or potassium.

40. The composition according to paragraph 39, wherein the rebaudioside to base ratio is from about 10:1 to 1:10 on molar basis.

41. The composition according to paragraph 36, wherein the rebaudioside to base ratio is from about 10:1 to 1:10 on molar basis.

42. The composition according to paragraph 37, wherein the rebaudioside to base ratio is from about 10:1 to 1:10 on molar basis.

43. The composition according to paragraph 38, wherein the rebaudioside to base ratio is from about 10:1 to 1:10 on molar basis.

44. The composition according to paragraph 39, wherein the rebaudioside to base ratio is from about 10:1 to 1:10 on molar basis.

The following paragraphs enumerated consecutively from 1 through 11 provide for additional various aspects of the present invention. In one embodiment, in a first paragraph (1), the present invention provides a mixture that consists essentially of stevia extract, wherein the mixture contain above 1% rebaudioside B (RB) by weight.

2. The mixture of paragraph 1, wherein the mixture contains about 1% to 30% RB by weight.

3. The mixture of paragraph 1 or 2, wherein the stevia extract has above 90% purity of total steviol glycosides.

4. The mixture of paragraph 3, wherein the stevia extract has above 95% purity of total steviol glycosides.

5. The mixture of paragraph 3 or 4, wherein total steviol glycosides contain rebaudioside A (RA) and/or rebaudioside D (RD).

6. The mixture of paragraph 5, wherein the ratio of RA to RB is from 70:30 to 99:1 by weight.

7. The mixture of paragraph 6, wherein the ratio of RA to RB is from 75:25 to 95:5 by weight.

8. The mixture of paragraph 7, wherein the ratio of RA to RB is from 80:20 to 95:5 by weight.

9. The mixture of paragraph 8, wherein the ratio of RA to RB is from 85:15 to 95:5 by weight.

10. The mixture of paragraph 9, wherein the ratio of RA to RB is about 90:10 by weight.

11. The mixture of paragraph 5-10, wherein the ratio of RD to RA is from 30:70 to 5:95 by weight.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Example 1 (KOH+RB)

10 g rebaudioside A, 100 mL potassium hydroxide and 100 mL methanol were blended and then refluxed for 1.5 hours. After the reaction mixture gradually returned to room temperature, the pH of the mixture was adjusted to 2.5 with an aqueous HCl solution (10%). With the addition of HCl, a white solid precipitated. During the time of reflux and through precipitation, continuous stirring as performed. When no additional solid precipitated, the reaction mixture was filtered and the filter cake was washed with distilled water. The solid was dried and 6.5 g white powder (rebaudioside B) was obtained. HPLC-MS spectrum showed 804.88, corresponding to the MW for RB.

At room temperature, 5 g rebaudioside B was mixed with 40 mL water with stirring to form a suspension. 3.5 mL of aqueous KOH (10%) was added to the suspension until the suspension became clear. The clear solution was poured into 200 mL acetone with stirring and a white solid gradually precipitated from solution. After filtration, the filter cake was washed with cold water and was dried. 4.0 g white powder was obtained as the potassium salt of rebaudioside B.

Example 2 (NaOH+RB)

10 g rebaudioside D, 20 mL sodium hydroxide and 100 mL ethanol were mixed and then heated at 70-90 degrees Celsius for 1.5 hours. After the reaction mixture gradually returned to room temperature, the pH of the mixture was adjusted to 3.0 by addition of HCl solution (10%). With the addition of HCl, a white solid precipitated while the solution was continuously stirred. When no additional solid precipitated, the reaction solution was filtered and the filter cake was washed with distilled water. The solid was dried and 6.7 g white powder (rebaudioside B) be obtained.

At room temperature, 5 g white powder (RB) was mixed with 40 mL water with stirring to form a suspension. 3.3 mL of aqueous NaOH (10%) was added to the suspension until the suspension became clear. The clear solution was dried by spray drying. About 4.0 g white powder (sodium salt of rebaudioside B) was obtained.

Example 3

The following examples indicate that salts of rebaudioside B can be dissolved in an acidic aqueous solution at high concentrations.

Sample preparation: Each sample was prepared by dissolving an appropriate amount of salt of Example 1, RA (if present) in a phosphate buffer solution having a pH of 2.7.

| Sample SN | Salt of Example 1 | Rebaudioside A | pH (phosphate buffer) |
|---|---|---|---|
| 2 | 300 ppm | 700 ppm | 2.7 |
| 3 | 400 ppm | 600 ppm | 2.7 |
| 5 | 500 ppm | none | 2.7 |

Maintained at 3.5-4.0° C.

Results of the Samples of Example 3

| Sample SN | Status within 0-5 min | Status after 5 hours | Status after 22 hours |
|---|---|---|---|
| 2 | Clear | Clear | Clear |
| 3 | Clear | Clear | Less white precipitate |
| 5 | White precipitate | White precipitate | White precipitate |

Example 4 ($K_2O$+RB)

0.1 mol Rebaudioside B and 0.1 mol $K_2O$ were added to water and then heated at 50 degree Celsius until the aqueous solution become clear. After drying, a white powder (potassium salt of rebaudioside B) be obtained by spray drying.

Example 5 ($K_2CO_3$+RB)

The procedure of Example 4 was followed with the replacement of $K_2O$ with $K_2CO_3$, to provide the potassium salt of rebaudioside B.

Example 6 ($KHCO_3$+RB)

The procedure of Example 4 was followed with the replacement of $K_2O$ with $KHCO_3$, to provide the potassium salt of rebaudioside B.

Example 7

Taste comparison between RB (prepared in Example 1, first part) and RA Purity of RA was 99.0% by HPLC and RB was 99.1% by HPLC.

HPLC Conditions
Instrument: Shimadzu SPD-20A
Mobile Phase: Acetonitrile-Water (Dissolve 25 mg ammonium acetate and 25 µL acetic acid into 200 mL water, filtered through 0.45 µm membrane)=80:20
Column: AgiLent Zorbax NH2 (5 µm, 4.6 mm×150 mm)
Flow: 1 mL/min
Temperature: Ambient
Wavelength: 210 nm
Sample Preparation: Weigh accurately 10 mg of sample into a 10 mL volumetric flask, add 5 mL mobile phase, stir till the solid dissolved, then add the mobile phase to volume.
Injection Volume: 10 µL
RB sample: 400 ppm aqueous solution
RA sample: 400 ppm aqueous solution Result: 7/10 experts found that RB had a lesser sweetness than RA, but also had less bitterness than RA. RA has a strong bitterness profile.

Generally it was found that RB has a similar taste profile with RA, especially with regard to sweetness. Because of less bitterness, RB tasted better than RA.

Example 8

Taste comparison between a mixture of RA/RB and RA. Purity of RA was 99.0% by HPLC and RB was 99.1% by HPLC.

RA/RB sample: RA 200 ppm+RB 200 ppm in aqueous solution

RA sample: RA 400 ppm in aqueous solution

Result: all experts fond that RA/RB had a diminished sweetness than RA alone, but difference was not significant. However, the RA/RB mixture had much less bitterness than the RA solution. The result showed that decreased bitterness contributed more to an improved taste profile.

Conclusion: all experts made the same judgment, which indicated there was a difference between the samples. However, the blend of RA/RB did not appreciably alter the sweetness profile, but improved bitterness by decreasing the bitterness of the solution in comparison to RA solution only.

Example 9

Purpose:

To evaluate the taste profile after addition of rebaudioside B (Reb B) to rebaudioside A (Reb A).

Materials:

Reb A, 97.2% (HPLC), provided by Ningbo Green-Health Pharmaceutical Co., Ltd.

Reb B, 99.3% (HPLC), provided by EPC Natural products Co., Ltd.

Sample Preparation:

Samples were an aqueous solution of Reb A and Reb B, or Reb A alone. The total concentration of Reb A and Reb B is set at 400 ppm. Environmental temperature was 20° C.

1) Details as shown below:

| Sample # | Reb A/Reb B (weight/weight) |
| --- | --- |
| 1 | 100% Reb A |
| 2 | 99:1 |
| 3 | 95:5 |
| 4 | 90:10 |
| 5 | 85:15 |
| 6 | 80:20 |
| 7 | 75:25 |
| 8 | 70:30 |

Results:

Nine persons were trained for sensory evaluation, and then underwent a multiple sensory evaluation. The tests provided that:

RB can remarkably affect the taste profile of RA.

From sample 1 to sample 4, below positive sensory profiles are getting stronger.

From sample 4 to sample 8, below negative sensory profile are becoming stronger.

Positive Sensory Profile:
to shorten the duration of onset of RA
to shorten the duration of lingering of RA
to reduce the bitterness and after taste Negative Sensory Profile:

With lowering bitterness, increased addition of Reb B brings more unpleasant taste, like metallic or astringent taste.

Increase of Reb B causes the total sweetness to decrease.

Conclusion:

The best ratio of Reb A to Reb B is 90:10 by weight.

The ratio of Reb A to Reb B (from 99:1 to 70:30) can provide a commercial application.

A preferred range is from about 75:25 to about 95:5 by weight. A more preferable range is from about 80:20 to about 95:5 by weight. When using a range from 85:15 to 95:5 by weight, the result is better.

Lastly, the experts determined the ratio of 90:10 was the best.

Example 10

When adding rebaudioside D (Reb D) to samples in example 9, keeping the total concentration of rebaudiosides at 400 ppm by adding water, the experts found Reb D can improve sensory taste profile under the same condition.

It was found that the ratio of RD to RA from 30:70 to 5:95 by weight, the blend of Reb A, B and D can provide a pleasant taste.

The addition of Reb D provided a better taste.

Example 11

According to examples 9 and 10, through adjusting the total concentration of rebaudiosides to make sensory evaluation, researchers of the present invention found that the suitable range of rebaudiosides concentration is from 100 ppm to 1000 ppm in aqueous solution. (Total of rebaudiosides is 100-1000 ppm, including RA+RB or RA+RB+RD) (Sample 4 was preferred from Example 9) In beverages, 400-600 ppm was found preferable.

Example 12

According to example 9, the RA (97.2% (HPLC), provided by Ningbo Green-Health Pharmaceutical Co., Ltd.) was replaced with below products (sample 1-7) provided by EPC Natural products Co., Ltd. to achieve the same sensory result.

| Sample No. | Product ID | product details |
| --- | --- | --- |
| 1 | SG95(RA50) | Total steviol glycosides: 95.52%; RA: 53.60%. |
| 2 | SG95(RA60) | Total steviol glycosides: 95.58%; RA: 63.14%. |
| 3 | SG95(RA80) | Total steviol glycosides: 96.02%; RA: 85.86%. |
| 4 | RA95 | RA: 95.54%. |
| 5 | RA97 | RA: 98.00%. |
| 6 | RA97S | RA: 97.46%; RD: 1.50%. |
| 7 | RA99 | RA: 99.48%. |

Samples 1-7 have different degree of aftertaste, but only slightly. When blended with RB under the conditions of example 9, shorter on-set, shorter lingering and less bitterness are noted by sensory evaluation. Samples 1-7 have acceptable profiles. In this case, addition of RB is a positive element to improve the general taste profile.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A stevia composition comprising a mixture of rebaudioside A and rebaudioside B, wherein the purity of the rebaudioside A is at least 95% pure, and the purity of rebaudioside B is at least 95% pure, wherein the ratio of rebaudioside A to rebaudioside B is from 99:1 to 70:30 by weight and rebaudioside C is absent from the mixture, and wherein the rebaudioside B is an amino acid salt of rebaudioside B.

2. The stevia composition of claim 1, wherein one or more components selected from the group consisting of rebaudioside D, E, F, stevioside, steviolmonoside, steviolbioside, rubusoside, and dulcoside are absent from the stevia composition.

3. The stevia composition of claim 1, wherein the mixture further contains rebaudioside D.

4. The stevia composition of claim 3, wherein the ratio of rebaudioside D to rebaudioside A is from 30:70 to 5:95 by weight.

* * * * *